(12) United States Patent
Tang et al.

(10) Patent No.: US 12,070,209 B2
(45) Date of Patent: Aug. 27, 2024

(54) MEDICAL DEVICE

(71) Applicant: EZISURG MEDICAL CO. LTD., Shanghai (CN)

(72) Inventors: Chuan Gang Tang, Shanghai (CN); Meng Hui Liao, Shanghai (CN); Ming Hui Bao, Shanghai (CN)

(73) Assignee: EZISURG MEDICAL CO. LTD., Shanghai (CN)

( * ) Notice: Subject to any disclaimer, the term of this patent is extended or adjusted under 35 U.S.C. 154(b) by 346 days.

(21) Appl. No.: 17/609,973

(22) PCT Filed: May 8, 2020

(86) PCT No.: PCT/CN2020/089155
§ 371 (c)(1),
(2) Date: Nov. 9, 2021

(87) PCT Pub. No.: WO2020/228600
PCT Pub. Date: Nov. 19, 2020

(65) Prior Publication Data
US 2022/0218343 A1    Jul. 14, 2022

(30) Foreign Application Priority Data
May 10, 2019   (CN) .......................... 201910390807.3

(51) Int. Cl.
*A61B 17/068*   (2006.01)
*A61B 17/072*   (2006.01)
*A61B 17/115*   (2006.01)

(52) U.S. Cl.
CPC ...... *A61B 17/07207* (2013.01); *A61B 17/115* (2013.01); *A61B 2017/07285* (2013.01)

(58) Field of Classification Search
CPC .............................................. A61B 17/07207
See application file for complete search history.

(56) References Cited

U.S. PATENT DOCUMENTS

| 5,865,361 A | 2/1999 | Milliman et al. |
| 2010/0243711 A1* | 9/2010 | Olson .............. A61B 17/07207 227/181.1 |

(Continued)

FOREIGN PATENT DOCUMENTS

| CN | 204379348 U | 6/2015 |
| CN | 105167814 A | 12/2015 |

(Continued)

OTHER PUBLICATIONS

International Search Report and Written Opinion in corresponding International Application No. PCT/CN2020/089155 mailed Jul. 29, 2020 (13 pages).

*Primary Examiner* — Eyamindae C Jallow
(74) *Attorney, Agent, or Firm* — Venable LLP

(57) ABSTRACT

A medical device includes an actuator, a connecting mechanism, and a control mechanism connected to the actuator by the connecting mechanism. The control mechanism includes a firing assembly, a limiting assembly connected to the firing assembly, and a reset mechanism connected to the limiting assembly. The firing assembly can move in a first direction after being fired to realize an action of the actuator. The limiting assembly can limit the firing assembly not to move in a second direction after the firing assembly moves in the first direction. After movement of the firing assembly is limited, the reset mechanism can adjust position of the limiting assembly to release the limit on the firing assembly and allow the firing assembly to move in the second direction. An operator can easily hold the medical device (e.g., a stapler) with one hand while completing a reset action of a firing rack.

19 Claims, 7 Drawing Sheets

(56) References Cited

U.S. PATENT DOCUMENTS

2013/0056522 A1* 3/2013 Swensgard ...... A61B 17/07292
                                                227/176.1
2014/0224686 A1* 8/2014 Aronhalt ............ A61B 17/0644
                                                 206/339

FOREIGN PATENT DOCUMENTS

| CN | 208031243 U | * 11/2018 |
| CN | 208031243 U | 11/2018 |
| CN | 210903169 U | 7/2020 |
| EP | 0324635 A1 | 7/1989 |

* cited by examiner

МЕDICAL DEVICE

CROSS-REFERENCE TO RELATED APPLICATIONS

This application is a U.S. National Stage application of PCT/CN2020/089155, filed May 8, 2020 and published on Nov. 19, 2020 as WO 2020/228600, which claims the benefit of Chinese Patent Application No. 201910390807.3 filed on May 10, 2019, all of which are hereby incorporated by reference in their entireties.

TECHNICAL FIELD

The present invention belongs to the technical field of medical devices, relates to a medical device, and more particularly to a medical device which can be reset with a manipulator.

BACKGROUND

In recent years, medical devices provided with a reset mechanism, for example staplers, have emerged on the market. Stapler is a surgical instrument, and its operating principle is to clamp tissues by closing front clamp portions, and then push out and compress metal staples in a staple cartridge of the stapler to suture the tissues together. In some staplers, a blade is also mounted at a clamp opening, and can incise the sutured tissues during tissue suturing.

FIG. 1 is a structural schematic view of a known stapler. With reference to FIG. 1, the stapler having the above functions includes an actuator 4, an intermediate connector, and a controller 2 (handle portion), wherein the handle portion includes a reset knob 31, and performs a reset operation by means of the reset knob 31.

Generally, a series of actions such as clamping tissues, pushing out staples, suturing, cutting tissue, blade withdrawal, and loosening tissue are realized mainly by means of the forward and backward movement of a center push rod of an intermediate connector; and the center push rod is connected to a firing rack of the handle portion at a back end.

The forward movement of the firing rack is completed by pulling a firing trigger and then driving the firing rack to move forward by a driving pawl on the trigger. The backward movement of the firing rack is completed by pulling back the reset knob on the firing rack and then driving the firing rack to move backward; the backward movement of the firing rack is also known as reset of the firing rack.

The actuator consists of an anvil assembly, a staple cartridge assembly, and a drive assembly. The anvil assembly includes a staple forming surface which is provided with multiple rows of staple grooves for forming metal staples. The staple cartridge assembly generally includes a staple cartridge, staples, a push block, a push slider, and a staple cartridge seat; an upper surface of the staple cartridge is a tissue contact surface; and the staple cartridge is mounted in the staple cartridge seat. A proximal end of the anvil assembly is movably connected to a proximal end of the staple cartridge assembly, and can switch between an open state and a closed state. The drive assembly is connected to a transmission mechanism, and is used to convert the action of the firing trigger into the actions of the actuator such as closing, firing, opening and the like. Generally, the anvil assembly and the staple cartridge seat further respectively include a longitudinal groove for the drive assembly to pass. When the drive assembly moves to a distal end of the actuator by means of the longitudinal groove, the anvil assembly and the staple cartridge assembly are driven to switch from the open state to the closed state, and the push slider and the push block are driven to push out a staple which is then formed in the staple groove on the staple forming surface of the anvil assembly. Generally, the drive assembly further includes a blade, wherein the blade is used to cut the tissue between multiple rows of staple lines after the tissue is sutured with the staple. The controller is used to manually control and operate the device, and generally includes a fixed handle, a firing trigger which is relatively movably connected to the fixed handle, a transmission mechanism for transferring an action of the firing trigger to the actuator, and a manual reset assembly. When the staple cartridge assembly and the anvil assembly of the actuator are in the closed state, the manual reset assembly can be operated to drive the staple cartridge assembly and the anvil assembly to restore the open state. The intermediate connector is movably connected to a distal end of the controller, and is connected to a proximal end of the actuator; the intermediate connector forms a connection channel for transferring the action of the firing trigger to the actuator.

When the known stapler resets the firing rack, an operator needs to pull back the reset knob with the other hand to complete reset. For example, in the U.S. Pat. No. 5,865,361, when the firing trigger of the stapler is fired, the anvil assembly and the staple cartridge assembly of the stapler is switched from the open state to the closed state, so as to clamp a target tissue. During a surgery, if a surgeon believes that the position at which the tissue is clamped needs to be adjusted, then the surgeon needs to pull back the manual reset assembly with the other hand, so as to drive the staple cartridge assembly and the anvil assembly to restore the open state. During a practical surgery, the target tissue of the stapler includes stomach, lung, large intestine and the like, wherein the stomach and the large intestine are generally thick, have a large number of wrinkles in tissue lumen, and may have incompletely separated adipose tissue on the surface; furthermore, there are a large number of alveoli in the lung tissue; therefore, when the actuator of the stapler closes and clamps the tissue for the first time, the tissue is generally difficult to be compressed to an ideal uniform thickness due to the thickness, wrinkles, and adipose tissue of the tissue or bubbles in the tissue. The phenomenon of nonuniform tissue compression due to the above factors can be effectively eliminated by repeatedly clamping the tissue at the same position; therefore, when the stapler subsequently drives a titanium staple to anastomose and cut the tissue, the titanium staple can be highly uniformly formed with a good anastomosis effect and a smooth tissue cutting edge. In order to repeatedly clamp the tissue at the same tissue position, the surgeon needs to loosen the device held by the other hand and repeatedly operate the firing trigger of the manual reset trigger of the stapler with two hands. In addition, after the actuator of the stapler correctly clamps the tissue and before the surgeon decides to staple and cut the tissue, firstly the surgeon needs to press a firing safety button of the stapler with the assistance of the other hand to open a firing safety apparatus, and then the surgeon can operate the firing trigger again to execute subsequent actions, which brings inconvenience to the operation of the device and causes extra risks to the surgery. During a minimally invasive surgery, the surgeon sometimes respectively operates different devices with two hands; if one device needs to be operated with two hands simultaneously, then the surgeon needs to firstly loosen the other held device. During a minimally invasive surgery, an in vitro controller of the device not controlled by the surgeon may displace during surgery due to an accidental touch; and a small amount of displacement of the device controller may cause a large amount of uncontrolled displacement of the actuator at a distal end of the device. The actuator at the distal end of the device is close to the tissue and organ in a target surgery region, and therefore the uncontrolled displacement of the actuator may damage the tissue and organ nearby. When the device does not need to be operated temporarily, some surgeons take the device out of the body to avoid a risk; and in some cases, the device is temporarily held by another surgeon; sometimes, the surgeon just loosen the device and press the distal end of the device against a tissue or in a gap between tissues. The actions either extend the surgery time or have the risk of damaging the tissue and organ.

In view of the existing status, a novel stapler is urgent to be designed to overcome the above various defects of the known staplers.

SUMMARY

The present invention provides a medical device which can be easily held by an operator with one hand while completing a reset action of the fired medical device.

In order to solve the above technical problem, according to one aspect of the present invention, the following technical solution is adopted:

A medical device, including an actuator, a connecting mechanism, and a control mechanism, wherein the control mechanism is connected to the actuator by means of the connecting mechanism;
- the control mechanism includes a firing assembly, a reset mechanism, and a limiting assembly;
- the firing assembly can move in a first direction after being fired, so as to realize a first action of the actuator;
- the limiting assembly is connected to the firing assembly, and can limit the firing assembly not to move in a second direction after the firing assembly moves a certain distance in the first direction;
- the reset mechanism is connected to the limiting assembly; and after the firing assembly is limited not to move in the second direction by the limiting assembly, the reset mechanism can adjust the position of the limiting assembly, such that the limiting assembly releases the limit on the firing assembly, and the firing assembly can move in the second direction.

As one embodiment of the present invention, the reset mechanism includes a reset switch and a transmission member; the limiting assembly includes a limiting slider; the transmission member is linked to the reset switch, and pokes the reset switch to a reset on position; the transmission member drives the limiting slider to move in a preset direction; and the limiting slider releases the limit on the firing assembly.

Further, the reset switch and the transmission member can be connected in an integrated manner or a split manner.

Further, the transmission member is a rotating structure or a sliding structure.

Further, the transmission member is a rotating structure; a first end of the rotating structure is linked to the reset switch, and pokes the reset switch to the reset on position; a second end of the rotating structure drives the limiting slider to move in the preset direction; and the limiting slider releases the limit on the firing assembly.

Further, the reset mechanism further includes an elastic member for the rotating structure; the limiting assembly further includes an elastic member for the limiting slider; the elastic member for the rotating structure is connected to the rotating structure; and the elastic member for the limiting slider is connected to the limiting slider.

Further, the elastic member for the rotating structure is a tension spring, and the elastic member for the limiting slider is a torsion spring.

As one embodiment of the present invention, the limiting assembly includes a limiting slider, a first elastic member, and a first elastic member for the reset switch; the reset mechanism includes a reset switch; a first end of the first elastic member is connected to the reset switch, and a second end is connected to the limiting slider, such that the first elastic member can act with the reset switch and the limiting slider in two directions; one end of the first elastic member for the reset switch presses the reset switch, and the other end is fixed on a corresponding structure of a housing; when the reset switch is poked to the reset on position, the reset switch is linked to the first end of the first elastic member; the first elastic member rotates a preset angle; the second end of the first elastic member pokes the limiting slider in a preset direction; and the limiting slider releases the limit on the firing assembly.

Further, the first elastic member is a torsion spring, and the first elastic member for the reset switch is a torsion spring.

As one embodiment of the present invention, the limiting assembly includes at least one limiting block; the limiting block is disposed on the reset mechanism; the reset mechanism includes a reset switch and a second elastic member for the reset switch; the firing assembly includes a rack provided with a limiting step; one end of the second elastic member for the reset switch acts on the reset switch, and the other end is fixed on a corresponding structure of a housing; the limiting block is clamped at the limiting step of the rack; when the reset switch is poked to the reset on position, the limiting block on the reset switch moves together to a non-limited position in the preset direction; and the limiting slider releases the limit on the firing assembly.

Further, the second elastic member for the reset switch is a compression spring.

As one embodiment of the present invention, the limiting assembly includes at least one limiting block; the limiting block is disposed on the reset mechanism; the reset mechanism includes a reset switch and a third elastic member for the reset switch; the firing assembly includes a rack provided with a limiting step; the limiting step occupies at least a certain width on a transverse first side; the limiting block is clamped at the limiting step of the rack; when the reset switch is poked to the reset on position, the limiting block on the reset switch translates together to a second side until the limiting block completely get out of the way of the limiting step on the rack.

Further, the third elastic member for the reset switch is a compression spring.

As one embodiment of the present invention, the control mechanism includes a pullback assembly; and the pullback assembly is connected to the firing assembly, and can apply a pullback force in the second direction to the firing assembly.

Further, the firing assembly includes a rack; a toothed side of the rack cooperates with a trigger assembly; the rack is provided with a pullback connection mechanism; and the pullback assembly cooperates with the pullback connection mechanism.

As one embodiment of the present invention, the firing assembly is a firing rack assembly; the firing rack assembly further includes a reset knob and a reset sheet; when the reset knob is applied with a preset pullback force, the reset knob drives the reset sheet to push aside the limiting slider; and the limiting slider releases the limit on the firing assembly.

As one embodiment of the present invention, the actuator includes a clamp, a blade component, and an elastic sheet of the clamp; the connecting mechanism includes a center push rod; the firing assembly includes a rack;

the center push rod is connected to the blade component; when the blade component is at a first position, the blade component presses on the clamp, such that the clamp can clamp the elastic sheet of the clamp; when the blade component is at a second position, the blade component does not press on the clamp, such that the clamp opens under the action of the elastic sheet of the clamp;

when the reset mechanism does a firing action, the center push rod, together with the rack, moves in the second direction; the center push rod is linked to the blade component; the blade component moves back until behind the clamp; and a stopper structure on the blade component does not press on the clamp, such that the clamp opens under the action of the elastic sheet of the clamp.

As one embodiment of the present invention, the actuator is a detachable reloader, or the actuator is connected to the connecting mechanism.

Further, the medical device includes a staple cartridge assembly; and the staple cartridge assembly is detachably mounted on a clamp of the actuator.

As one embodiment of the present invention, the medical device is a stapler.

The present invention has the following beneficial effects: an operator can easily hold the medical device (for example, a stapler) provided by the present invention with one hand while completing a reset action of a firing rack.

DETAILED DESCRIPTION OF THE EMBODIMENTS

Figure 1:
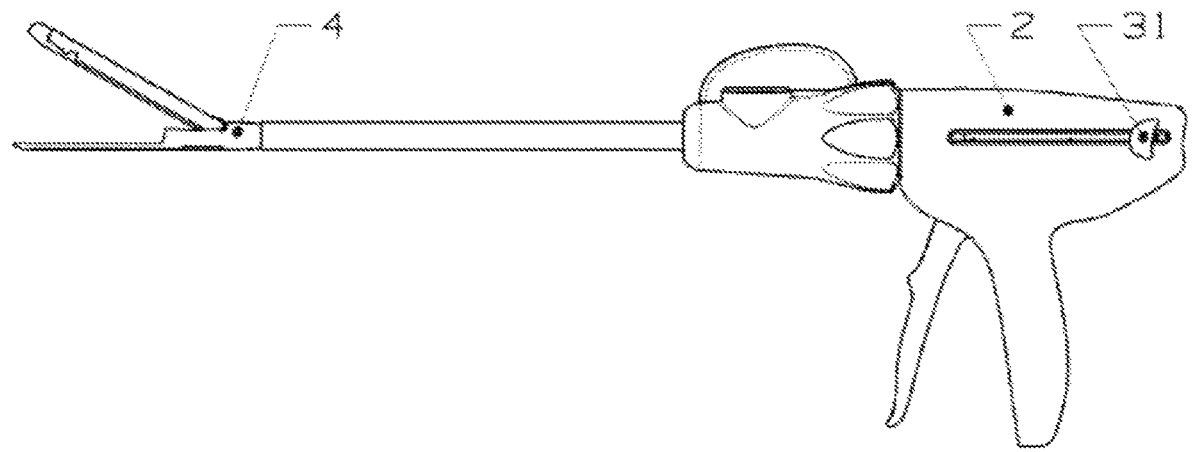
FIG. 1 is a structural schematic view of a known stapler.

The preferred embodiments of the present invention will be described in detail hereafter with reference to the accompanying drawings.

In order to further understand the present invention, the preferred implementation solutions of the present invention will be described hereafter in combination with the embodiments. However, it should be understood that the descriptions are only intended to further describe the features and advantages of the present invention, but not to limit the claims of the present invention.

The following descriptions are provided on the basis of a few typical embodiments, and the present invention is not only limited to the scope described by the embodiments. Mutual substitutions of the same or similar means in the prior art with the technical features in the embodiments are also in the protection scope of the present invention.

Similar reference signs in the drawings and the following description denote similar or the same elements. According to usual practice, the term "proximal end" refers to the end of the device close to the operator during use, and the term "distal end" refers to the end of the device distal from the operator.

The present invention discloses a medical device, including an actuator, a connecting mechanism, and a control mechanism, wherein the control mechanism is connected to the actuator by means of the connecting mechanism; the control mechanism includes a firing assembly, a reset mechanism, and a limiting assembly; the firing assembly can move in a first direction after being fired, so as to realize a first action of the actuator; the limiting assembly is connected to the firing assembly, and can limit the firing assembly not to move in a second direction after the firing assembly moves a certain distance in the first direction; the reset mechanism is connected to the limiting assembly; and after the firing assembly is limited not to move in the second direction by the limiting assembly, the reset mechanism can adjust the position of the limiting assembly, such that the limiting assembly releases the limit on the firing assembly, and the firing assembly can move in the second direction.

In one embodiment of the present invention, the first direction is the direction from the center of the firing assembly to the distal end, and the second direction is the direction from the center of the firing assembly to the proximal end. The first action of the actuator is the clamping action of the actuator (the first action can also be an opening action; the first action and the reset action can be designed according to requirements).

Figure 2:
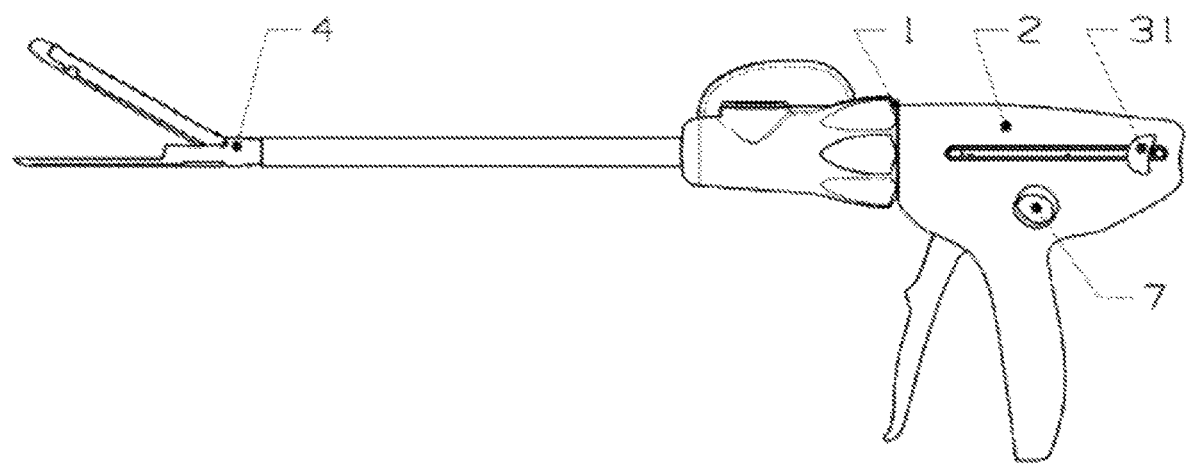
FIG. 2 is a structural schematic view of a stapler according to one embodiment of the present invention.

FIG. 2 is a structural schematic view of a stapler according to one embodiment of the present invention. With reference to FIG. 2, in one embodiment of the present invention, the medical device is a stapler 1; the stapler 1 includes an end effector 4 (equivalent to the actuator), an intermediate connector 5 (equivalent to the connecting mechanism), and a handle portion 2 (equivalent to the control mechanism) located at the back end, wherein the handle portion includes a firing rack assembly 3, a reset mechanism, and a limiting assembly. In one embodiment of the present invention, the reset mechanism includes a reset switch 70, wherein the form of the reset switch 7 is not limited to button, and the position thereof is not limited to lateral surface or back end. The reset switch 7 is switched from off to on; the limiting assembly linked to the reset switch 7 releases the limit on the firing rack assembly 3, such that the firing rack assembly 3 resets.

In one embodiment of the present invention, the reset mechanism includes a reset switch and a transmission member; the limiting assembly includes a limiting slider; the transmission member is linked to the reset switch, and pokes the reset switch to a reset on position; the transmission member moves the limiting slider in a preset direction; and the limiting slider releases the limit on the firing assembly. In one embodiment, the reset mechanism further includes an elastic member for the rotating structure; the limiting assembly further includes an elastic member for the limiting slider; the elastic member for the rotating structure is connected to the rotating structure; and the elastic member for the limiting slider is connected to the limiting slider.

Further, the reset switch and the transmission member can be connected in an integrated manner or a split manner.

In one embodiment of the present invention, the actuator includes a clamp, a blade component, and an elastic sheet of the clamp; the connecting mechanism includes a center push rod; the firing assembly includes a rack; the center push rod is connected to the blade component; when the blade component is at a first position, the blade component presses on the clamp, such that the clamp can clamp the elastic sheet of the clamp; when the blade component is at a second position, the blade component does not press on the clamp, such that the clamp opens under the action of the elastic sheet of the clamp; when the reset mechanism does a firing action, the center push rod, together with the rack, also moves in the second direction; the center push rod is linked to the blade component; the blade component moves back until behind the clamp; and a stopper structure on the blade component does not press on the clamp, such that the clamp opens under the action of the elastic sheet of the clamp.

In one embodiment, the transmission member is a rotating structure.

Figure 3:
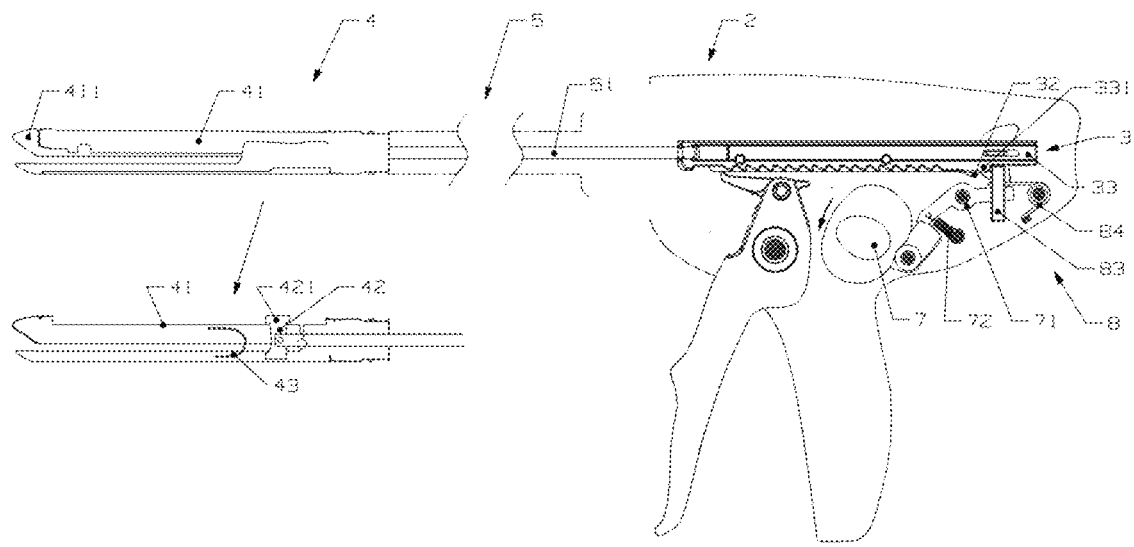
FIG. 3 is a structural schematic view of the stapler (which is in a state before a reset and performs a reset operation by means of a reset switch) according to one embodiment of the present invention.

FIG. 3 is a structural schematic view of the stapler (which is in a state before a reset and performs a reset operation by means of a reset switch) according to one embodiment of the present invention. With reference to FIG. 3, in one embodiment of the present invention, the firing rack assembly 3 includes a rack 33. The reset mechanism includes a reset switch 7, a rotation sheet 71, and a tension spring 72 for the rotation sheet. The front end actuator 4 includes a clamp 41, a blade component 42, and an elastic sheet 43 of the clamp; and a staple cartridge 411 on the clamp 41 can be a fixed staple cartridge or a detachable staple cartridge. The limiting assembly 8 includes a limiting slider 83 and a torsion spring 84 for the limiting slider; the tension spring 72 for the rotation sheet is connected to the rotation sheet 71, and the torsion spring 84 for the limiting slider is connected to the limiting slider 83.

Figure 4:
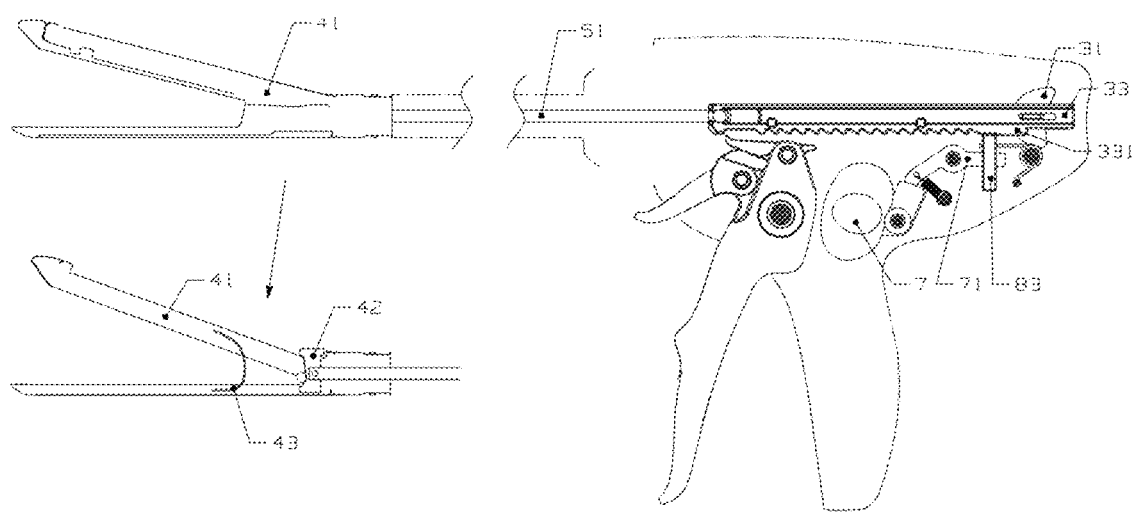
FIG. 4 is a structural schematic view of the stapler (which is in a state after a reset) according to one embodiment of the present invention.

In one embodiment of the present invention, the reset switch 7 performs a reset operation; the interaction relationships of the assembly components of the stapler are as follows:

As shown in FIG. 3, when the reset switch 7 in FIG. 3 is in an off state, the clamp 41 is in a clamping state; when the reset switch 7 is anticlockwise pocked by a preset angle to the reset on position, the reset switch 7 is linked to a left end of the rotation sheet 71; the rotation sheet 71 clockwise rotates a preset angle; a right end of the rotation sheet 71 presses down the limiting slider 83 to get out of the way of a corresponding limiting step 331 on the rack 33; the rack 33 is applied with a pullback force and is pulled to reset; the center push rod 51 also moves back together with the rack 33; the center push rod 51 is linked to the blade component 42; the blade component 42 moves back until behind the clamp 41; and a stopper structure 421 on the blade component 42 does not press on the clamp 41, such that the clamp 41 opens under the action of the elastic sheet 43 of the clamp. As shown in FIG. 4, when the reset switch 7 is in an on state, the clamp 41 is in an open state, wherein the tension spring 82 for the rotation sheet and the torsion spring 84 for the limiting slider provide a limit retaining force for the limiting assembly 8.

Figure 13:
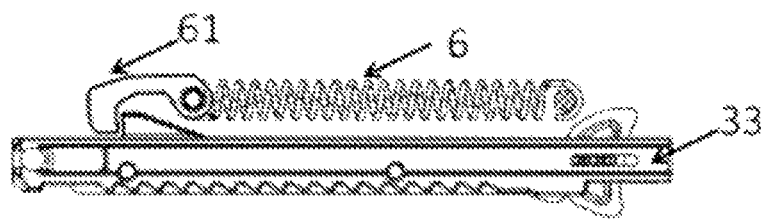
FIG. 13 is a structural schematic view of a pullback assembly of the stapler according to one embodiment of the present invention.

As shown in FIG. 13, in one embodiment, the handle portion further includes a pullback assembly 6. One end of the pullback assembly 6 is connected to the firing rack assembly 3, and the other end is fixed on a corresponding structure of the housing, and can apply a pullback force in a second direction to the firing assembly. With reference to FIGS. 3 and 13, when the reset switch 7 is anticlockwise poked by a preset angle to the reset on position, the right end of the rotation sheet 71 presses down the limiting slider 83 to get out of the way of the limiting step 331 on the rack 33; and the rack 33 is pulled to reset under the action of a rack stopper 61.

Figure 5:
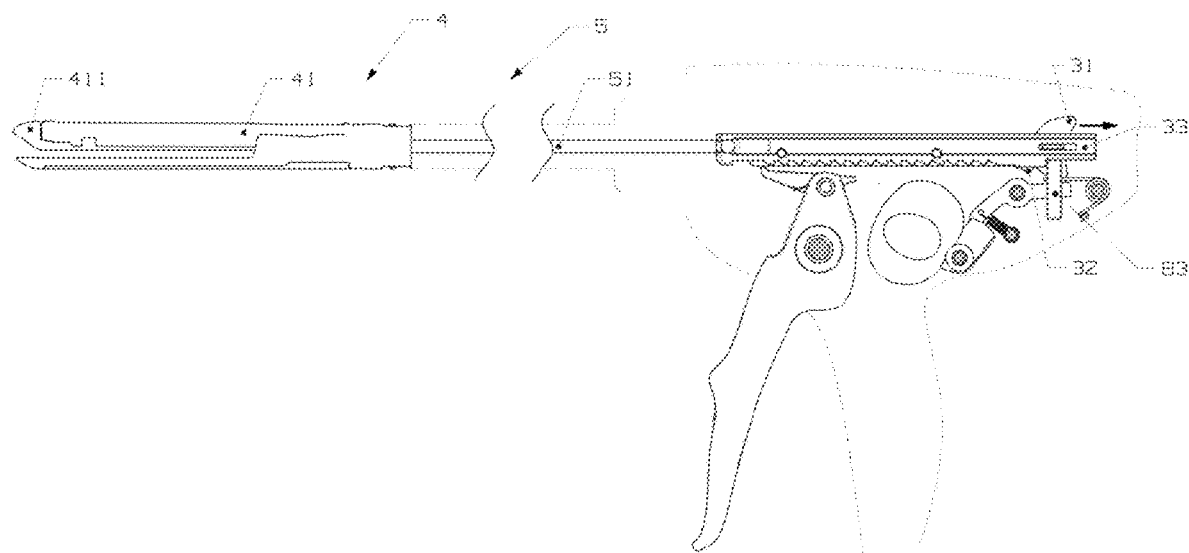
FIG. 5 is a structural schematic view of the stapler (which is in a state before a reset and performs a reset operation by means of a reset knob) according to one embodiment of the present invention.

FIG. 5 is a structural schematic view of the stapler (which is in a state before a reset and performs a reset operation by means of a reset knob) according to one embodiment of the present invention. With reference to FIG. 5, in another embodiment of the present invention, the firing rack assembly 3 includes a reset knob 31, a reset sheet 32, and a rack 33, and can perform a reset operation by means of the reset knob 31; the interaction relationships of the assembly components are as follows: the reset knob 31 is pulled back, and drives the reset sheet 32 to push aside the limiting slider 83 which presses down the limiting assembly 8; and the firing rack assembly 3 is manually pulled back to reset.

In one embodiment, the transmission member is a sliding structure.

Figure 15:
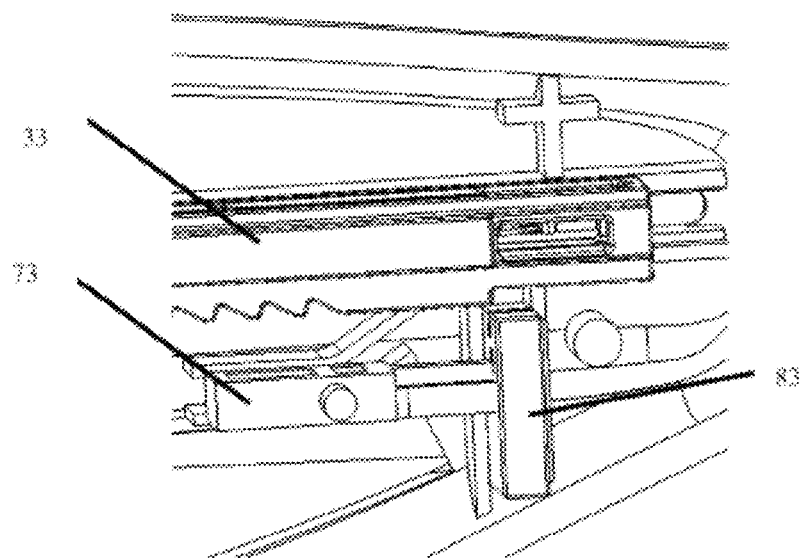
FIG. 15 is a structural schematic view of a transmission member (which is a sliding structure) of the stapler according to one embodiment of the present invention.

As shown in FIG. 15, the transmission member is, for example, a sliding structure 73. One end of the sliding structure 73 is connected to the reset switch, and the other end is connected to the limiting slider 83. When the reset switch is poked, the sliding structure 73 can slide along a preset track. The sliding structure can slide along a preset track, for example, a straight line or a curve. When the sliding structure 73 moves the limiting slider 83 in the preset direction, the limiting slider gets out of the way of the limiting step 331 on the rack 33, and the limiting slider 83 releases the limit on the firing assembly.

In one embodiment of the present invention, the limiting assembly includes a limiting slider, a first elastic member, and a first elastic member for the reset switch; the reset mechanism includes a reset switch; a first end of the first elastic member is connected to the reset switch, and a second end is connected to the limiting slider, such that the first elastic member can act with the reset switch and the limiting slider in two directions; one end of the first elastic member for the reset switch presses the reset switch, and the other end is fixed on a corresponding structure of a housing; when the reset switch is poked to the reset on position, the reset switch is linked to the first end of the first elastic member; the first elastic member rotates a preset angle; the second end of the first elastic member pokes the limiting slider in a preset direction; and the limiting slider releases the limit on the firing assembly. The first elastic member for the reset switch provides a retaining force for remaining the reset switch at a limited position; and the first elastic member also provides a remaining force for remaining the reset switch at the limited position.

Figure 6:
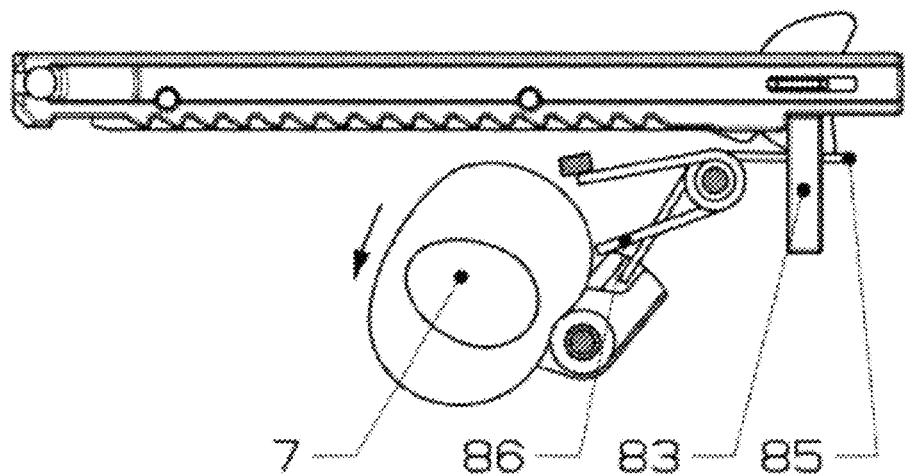
FIG. 6 is a structural schematic view of a limiting assembly of the stapler (which is in a state before a reset) according to one embodiment of the present invention.
Figure 7:
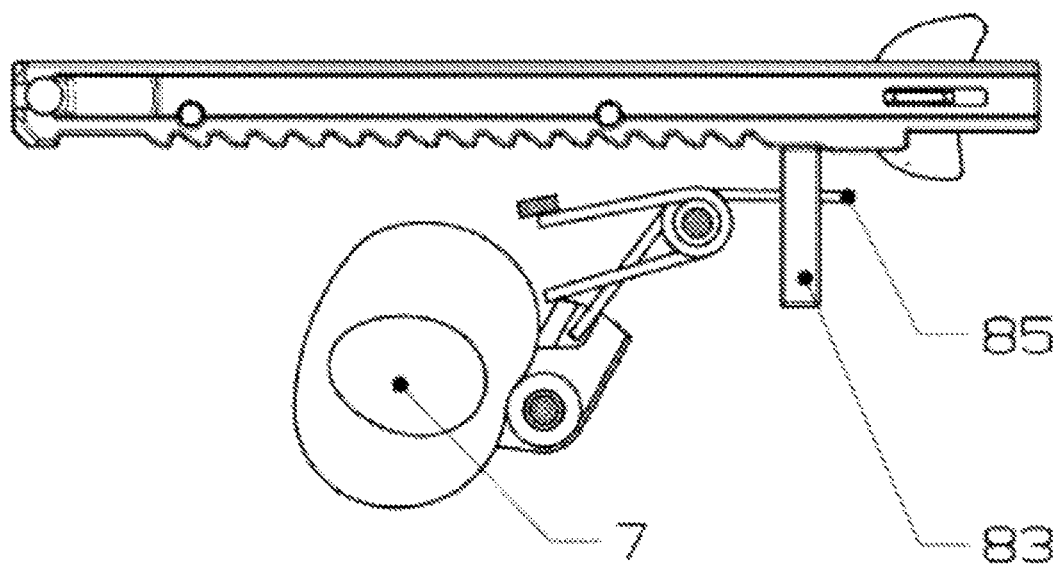
FIG. 7 is a structural schematic view of the limiting assembly of the stapler (which is in a state after a reset) according to one embodiment of the present invention.

FIG. 6 is a structural schematic view of the limiting assembly of the stapler (which is in a state before a reset) according to one embodiment of the present invention; and FIG. 7 is a structural schematic view of the limiting assembly of the stapler (which is in a state after a reset) according to one embodiment of the present invention. With reference to FIG. 6-7, in one embodiment of the present invention, the limiting assembly 8 includes a limiting slider 83, a first elastic member 85, and a first elastic member 86 for the reset switch, wherein a left end of the first elastic member 85 is inserted into the reset switch 7, and a right end is inserted into the limiting slider 83, such that the first elastic member 85 can act with the reset switch 7 and the limiting slider 83 in two directions; one end of the first elastic member 86 for the reset switch presses the reset switch 7, and the other end is fixed on a corresponding structure of a housing. The interaction relationships of the assembly components of the limiting assembly 8 are as follows: when the reset switch 7 is anticlockwise poked by a preset angle to the reset on position, the reset switch 7 is linked to the left end of the first elastic member 85; and when the first elastic member 85 clockwise rotates a preset angle, the right end of the first elastic member 85 pokes downward the limiting slider 83, wherein the first elastic member 86 for the reset switch provides a retaining force for remaining the reset switch 7 at a limited position; and the first elastic member 85 also provides a remaining force for remaining the reset switch 7 at the limited position. In one embodiment, the first elastic member 85 is a torsion spring, and the first elastic member 86 for the reset switch is a torsion spring.

In one embodiment of the present invention, the limiting assembly includes at least one limiting block; the limiting block is disposed on the reset mechanism; the reset mechanism includes a reset switch and a second elastic member for the reset switch; the firing assembly includes a rack provided with a limiting step; one end of the second elastic member for the reset switch acts on the reset switch, and the other end is fixed on a corresponding structure of a housing; the limiting block is clamped at the limiting step of the rack; when the reset switch is poked to the reset on position, the limiting block on the reset switch moves together to a non-limited position in the preset direction; and the limiting slider releases the limit on the firing assembly. The second elastic member for the reset switch provides a retaining force for remaining the reset switch at the limited position.

Figure 8:
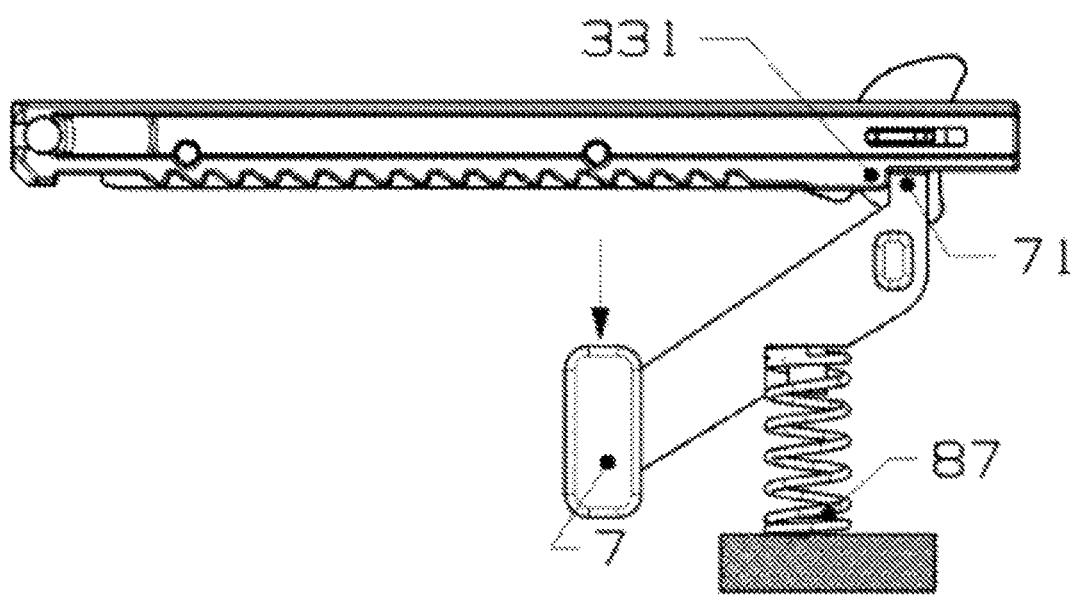
FIG. 8 is a structural schematic view of the limiting assembly of the stapler (which is in a state before a reset) according to one embodiment of the present invention.
Figure 9:
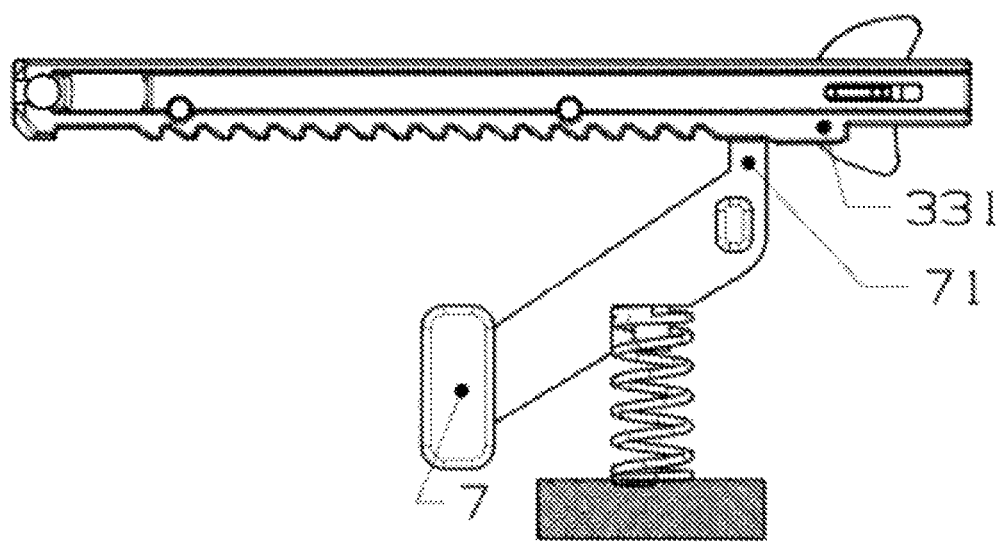
FIG. 9 is a structural schematic view of the limiting assembly of the stapler (which is in a state after a reset) according to one embodiment of the present invention.

FIG. 8 is a structural schematic view of the limiting assembly of the stapler (which is in a state before a reset) according to one embodiment of the present invention; and FIG. 9 is a structural schematic view of the limiting assembly of the stapler (which is in a state after a reset) according to one embodiment of the present invention. The limiting assembly is a limiting block 71, and the limiting block 71 is disposed on the reset mechanism. The limiting block 71 is disposed corresponding to the limiting step 331 on the rack 33. The reset mechanism includes a reset switch 7 and a second elastic member 87 for the reset switch. One end of the second elastic member 87 for the reset switch acts on the reset switch 7, and the other end is fixed on a corresponding structure of a housing. As shown in FIG. 8, the limiting block 71 is clamped at the limiting step 331 of the rack 33. When the reset switch 7 is poked downward a certain distance to the reset on position, the limiting structure 71 together moves downward to the non-limited position, as shown in FIG. 9. The second elastic member 87 for the reset switch provides a retaining force for remaining the reset switch 7 at the limited position. In one embodiment, the second elastic member 87 for the reset switch is a compression spring.

In one embodiment of the present invention, the limiting assembly includes at least one limiting block; the limiting block is disposed on the reset mechanism; the reset mechanism includes a reset switch and a third elastic member for the reset switch; the firing assembly includes a rack provided with a limiting step; the limiting step occupies at least a certain width on a transverse first side; the limiting block is clamped at the limiting step of the rack; when the reset switch is poked to the reset on position, the limiting block on the reset switch translates together to a second side until the limiting block completely get out of the way of the limiting step on the rack. The third elastic member for the reset switch provides a retaining force for remaining the reset switch at the limited position.

Figure 10:
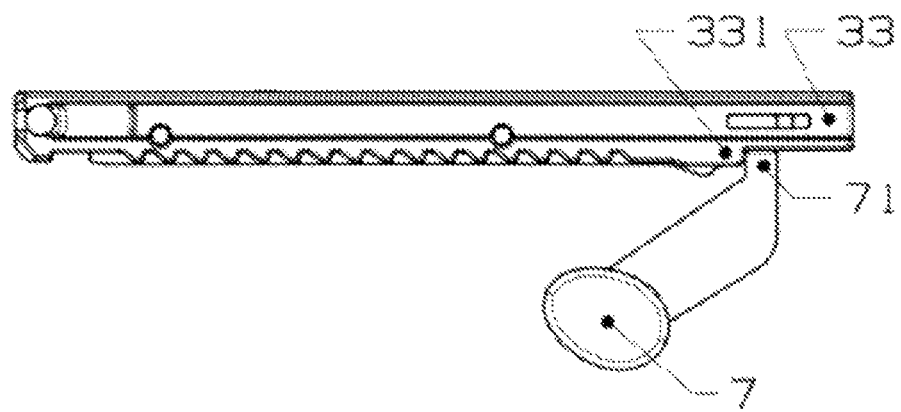
FIG. 10 is a structural schematic view (front view) of the limiting assembly of the stapler (which is in a state before a reset) according to one embodiment of the present invention.
Figure 11:
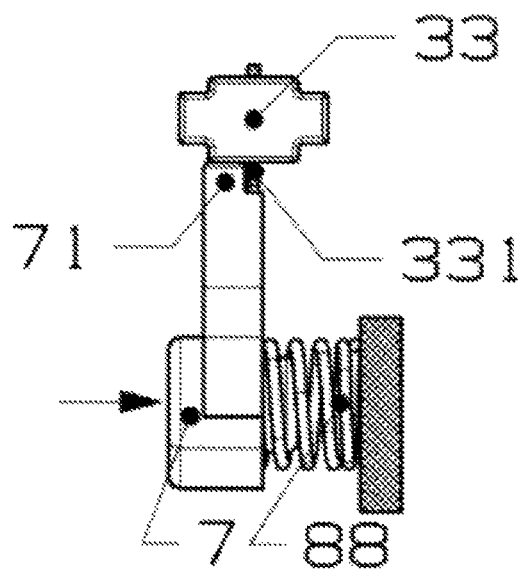
FIG. 11 is a structural schematic view (side view) of the limiting assembly of the stapler (which is in a state before a reset) according to one embodiment of the present invention.
Figure 12:
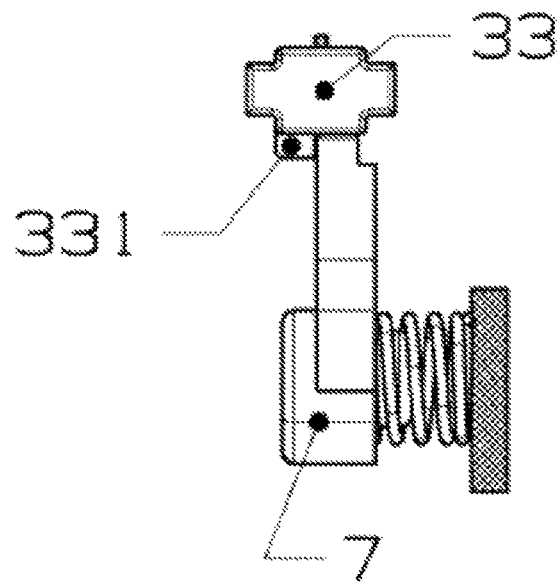
FIG. 12 is a structural schematic view of the limiting assembly of the stapler (which is in a state after a reset) according to one embodiment of the present invention.

FIG. 10-12 are structural schematic view of the limiting assembly of the stapler according to one embodiment of the present invention. With reference to FIG. 10-12, in one embodiment of the present invention, the limiting assembly is a limiting block 71, and the limiting block 71 is disposed on the reset mechanism. The reset mechanism includes a reset switch 7 and a third elastic member 88 for the reset switch (the reset switch 7 can also be independent from the limiting assembly 8). The limiting block 71 is disposed corresponding to the limiting step 331 on the rack 33. As shown in FIG. 11, the limiting block 71 is clamped at the limiting step 331 of the rack 33. When the reset switch 7 is pressed down to the reset on position, the limiting block 71 together translates rightward (equivalent to that an upper limiting block together translates to a second side) until the limiting block completely gets out of the way of the limiting step 331 on the rack 33, and the limiting step 331 occupies a certain width of a transverse left side (equivalent to that the limiting step occupies a certain width of a transverse first side), as shown in FIG. 12. The third elastic member 88 for the reset switch provides a retaining force for remaining the reset switch 7 at the limited position. In one embodiment, the third elastic member 88 for the reset switch is a compression spring.

Figure 14:
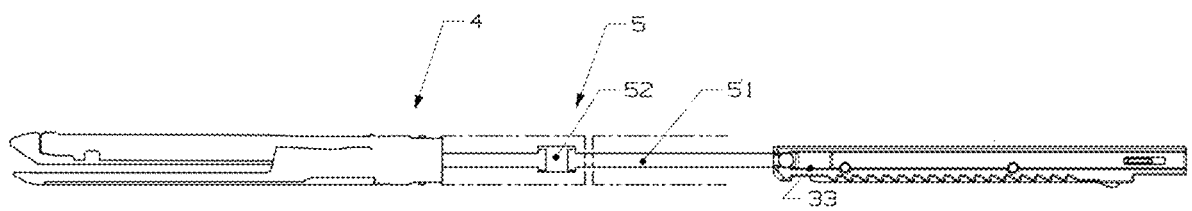
FIG. 14 is a structural schematic view of an actuator of the stapler according to one embodiment of the present invention.

FIG. 14 is a structural schematic view of an actuator of the stapler according to one embodiment of the present invention. With reference to FIG. 14, in one embodiment of the present invention, the actuator 4 is a reloader (for example, a stable box), and is detachably connected to the intermediate connector 5. In another embodiment, the actuator is an end actuator, and is connected to the intermediate connector 5 (not shown in the figure). In one embodiment, the staple cartridge assembly is detachably mounted on a clamp of the actuator.

In summary, an operator can easily hold the medical device (for example, a stapler) provided by the present invention with one hand while completing a reset action of a firing rack.

The technical features of the above embodiments can be combined at will. In order to enable the descriptions to be concise, all the possible combinations of the technical features in the above embodiments are not described. However, the combinations of the technical features, as long as the combinations do not conflict, should be all concluded in the scope recorded in the description.

The above descriptions and applications of the present invention are descriptive, but not intended to limit the scope of the present invention in the above embodiments. The variations and changes of the embodiments disclosed herein are possible, and various substitutions and equivalent components of the embodiments are commonly known for a person skilled in the art. A person skilled in the art should understand that the present invention can be implemented in other forms, structures, arrangements, proportions, and other assemblies, materials, and components without departing from the spirit or essential features of the present invention. The embodiments disclosed herein may have other variations and changes without departing from the scope and spirit of the present invention.

The invention claimed is:

1. A medical device, comprising an actuator, a connecting mechanism, and a control mechanism, wherein the control mechanism is connected to the actuator by means of the connecting mechanism;
   the control mechanism comprises a firing assembly, a reset mechanism, and a limiting assembly;
   the firing assembly is configured to move in a first direction after being fired, so as to realize a first action of the actuator;
   the limiting assembly is connected to the firing assembly, and is configured to limit the firing assembly not to move in a second direction after the firing assembly moves a certain distance in the first direction;
   the reset mechanism is connected to the limiting assembly; and after the firing assembly is limited not to move in the second direction by the limiting assembly, the reset mechanism is configured to adjust the position of the limiting assembly, such that the limiting assembly releases the limit on the firing assembly to allow the firing assembly to move in the second direction.

2. The medical device according to claim 1, wherein the reset mechanism comprises a reset switch and a transmission member; the limiting assembly comprises a limiting slider; and
   the transmission member is linked to the reset switch, and pokes the reset switch to a reset on position; the transmission member drives the limiting slider to move in a preset direction; and the limiting slider releases the limit on the firing assembly.

3. The medical device according to claim 2, wherein the transmission member is a rotating structure or a sliding structure.

4. The medical device according to claim 2, wherein the transmission member is a rotating structure; a first end of the rotating structure is linked to the reset switch, and pokes the reset switch to the reset on position; a second end of the rotating structure drives the limiting slider to move in the preset direction; and the limiting slider releases the limit on the firing assembly.

5. The medical device according to claim 2, wherein the reset mechanism further comprises an elastic member for the rotating structure; the limiting assembly further comprises an elastic member for the limiting slider; the elastic member for the rotating structure is connected to the rotating structure; and the elastic member for the limiting slider is connected to the limiting slider.

6. The medical device according to claim 5, wherein the elastic member for the rotating structure is a tension spring, and the elastic member for the limiting slider is a torsion spring.

7. The medical device according to claim 2, wherein the firing assembly is a firing rack assembly; the firing rack assembly further comprises a reset knob and a reset sheet; when the reset knob is applied with a preset pullback force, the reset knob drives the reset sheet to push aside the limiting slider; and the limiting slider releases the limit on the firing assembly.

8. The medical device according to claim 7, wherein the medical device comprises a staple cartridge assembly; and the staple cartridge assembly is detachably mounted on a clamp of the actuator.

9. The medical device according to claim 1, wherein the limiting assembly comprises a limiting slider, a first elastic member, and a first elastic member for the reset switch; the reset mechanism comprises a reset switch;
   a first end of the first elastic member is connected to the reset switch, and a second end is connected to the limiting slider, such that the first elastic member can act with the reset switch and the limiting slider in two directions; one end of the first elastic member for the reset switch presses the reset switch, and the other end is fixed on a corresponding structure of a housing; and
   when the reset switch is poked to the reset on position, the reset switch is linked to the first end of the first elastic member; the first elastic member rotates a preset angle; the second end of the first elastic member pokes the limiting slider in a preset direction; and the limiting slider releases the limit on the firing assembly.

10. The medical device according to claim 9, wherein the first elastic member is a torsion spring, and the first elastic member for the reset switch is a torsion spring.

11. The medical device according to claim 9, wherein the firing assembly is a firing rack assembly; the firing rack assembly further comprises a reset knob and a reset sheet; when the reset knob is applied with a preset pullback force, the reset knob drives the reset sheet to push aside the limiting slider; and the limiting slider releases the limit on the firing assembly.

12. The medical device according to claim 1, wherein the limiting assembly comprises at least one limiting block; the limiting block is disposed on the reset mechanism; the reset mechanism comprises a reset switch and a second elastic member for the reset switch; the firing assembly comprises a rack provided with a limiting step;
   one end of the second elastic member for the reset switch acts on the reset switch, and the other end is fixed on a corresponding structure of a housing; the limiting block is clamped at the limiting step of the rack; and
   when the reset switch is poked to the reset on position, the limiting block on the reset switch moves together to a non-limited position in the preset direction; and the limiting slider releases the limit on the firing assembly.

13. The medical device according to claim 12, wherein the second elastic member for the reset switch is a compression spring.

14. The medical device according to claim 1, wherein the limiting assembly comprises at least one limiting block; the limiting block is disposed on the reset mechanism; the reset mechanism comprises a reset switch and a third elastic member for the reset switch;

the firing assembly comprises a rack provided with a limiting step; the limiting step occupies at least a certain width on a transverse first side;

the limiting block is clamped at the limiting step of the rack; and when the reset switch is poked to the reset on position, the limiting block on the reset switch translates together to a second side until the limiting block completely get out of the way of the limiting step on the rack.

15. The medical device according to claim 14, wherein the third elastic member for the reset switch is a compression spring.

16. The medical device according to claim 1, wherein the control mechanism comprises a pullback assembly; and the pullback assembly is connected to the firing assembly, and is configured to apply a pullback force in the second direction to the firing assembly.

17. The medical device according to claim 16, wherein the firing assembly comprises a rack; a toothed side of the rack cooperates with a trigger assembly; the rack is provided with a pullback connection mechanism; and the pullback assembly cooperates with the pullback connection mechanism.

18. The medical device according to claim 1, wherein the actuator comprises a clamp, a blade component, and an elastic sheet of the clamp; the connecting mechanism comprises a center push rod; the firing assembly comprises a rack;

the center push rod is connected to the blade component; when the blade component is at a first position, the blade component presses on the clamp, such that the clamp can clamp the elastic sheet of the clamp; when the blade component is at a second position, the blade component does not press on the clamp, such that the clamp opens under the action of the elastic sheet of the clamp; and when the reset mechanism does a firing action, the center push rod, together with the rack, moves in the second direction; the center push rod is linked to the blade component; the blade component moves back until behind the clamp; and a stopper structure on the blade component does not press on the clamp, such that the clamp opens under the action of the elastic sheet of the clamp.

19. The medical device according to claim 1, wherein the actuator is a detachable reloader, or the actuator is connected to the connecting mechanism.

* * * * *